United States Patent [19]

Fabricant

[11] Patent Number: 4,585,454
[45] Date of Patent: Apr. 29, 1986

[54] INTRAOCULAR LENS DEVICE

[76] Inventor: Robert N. Fabricant, 285 E. 24th St., Upland, Calif. 91786

[21] Appl. No.: 581,727

[22] Filed: Feb. 21, 1984

[51] Int. Cl.⁴ .............................................. A61F 2/16
[52] U.S. Cl. ....................................................... 623/6
[58] Field of Search ................................... 3/13; 623/6

[56] References Cited

U.S. PATENT DOCUMENTS 4,244,060  1/1981  Hoffer ........................................ 3/13
4,527,294  7/1985  Heslin ....................................... 623/6

OTHER PUBLICATIONS

The Hoffer Ridge Lenses from Cilco, brochure from Cilco, Inc. 1616 13th Ave., Box 1680, Huntington, West Va., 25717, 6 pages, Mar. 1983.

Primary Examiner—Ronald L. Frinks
Attorney, Agent, or Firm—John G. Mesaros

[57] ABSTRACT

An intraocular lens device having a generally planoconvex optic with first and second haptics secured at generally diametrically opposed positions, the haptics being resilient. The posterior surface of the optic is provided with means for selectively releasably retaining the haptics in an inwardly flexed condition just prior to insertion in the patient's eye, the means taking the form of shoulders or slots. After insertion the haptics may be released by a spatula, or alternatively, the optic may be provided with through holes in proximity to the shoulders or slots for enabling insertion of a tool therethrough from the anterior of the device for disengagement of the haptics.

15 Claims, 4 Drawing Figures

INTRAOCULAR LENS DEVICE

BACKGROUND OF THE INVENTION

The background of the invention will be discussed in two parts:

FIELD OF THE INVENTION

This invention relates to intraocular lens devices, and more particularly to such a lens having means for selectively retaining the haptic thereof in a withdrawn position during insertion.

DESCRIPTION OF THE PRIOR ART

Cataract removal is often accompanied, where feasible, by implantation of an artificial lens referred to as an intraocular lens. There are numerous intraocular lens devices available, with most lenses having certain common elements, these being the lens, or optic, which has drill holes passing axially therethrough, adjacent the perimeter for enabling positioning of the lens after insertion, the lenses also including haptics, which are generally resilient attachment and positioning members extending out from the lens, generally in the plane of the lens.

One such intraocular lens is known as the Shearing lens, in which the haptics are of J-shaped configuration, formed of a polypropylene material which has a slight degree of resilience. During insertion of this lens, or the other similar type lenses, the haptics extending from the diametrically opposed edges increase the overall maximum dimension of the lens device.

In cataract surgery, the clouded lens of the eye is removed. The lens is located behind the iris within an envelope referred to as the capsule. During insertion of an intraocular lens device, the device must be passed through the pupil of the iris, which, depending on whether it is dilated or not, may vary in diameter. Insertion of the intraocular lens device is sometimes difficult, with the additional length of the device occasioned by the haptics being a contributing factor. In some instances, particularly when the pupil is not dilated, surgical instruments must be utilized to grip the iris to enlarge the opening, thus potentially inducing trauma to the so-gripped portion.

Some lens devices currently available are provided with a peripheral shoulder portion on the posterior side thereof to act as a spacer between the capsule surface and the posterior of the optic portion of the lens device.

It is an object of the present invention to provide a new and improved intraocular lens device.

It is another object of the present invention to provide a new and improved intraocular lens device having haptics which may be captively retained by means on the optic during insertion.

It is a further object of the present invention to provide a new and improved intraocular lens device which has means for captively retaining the haptic during insertion of the lens device and means for readily disengaging the haptic after insertion.

SUMMARY OF THE INVENTION

The foregoing and other objects of the invention are accomplished by providing an introcular lens device having a generally plano-convex optic portion with first and second diametrically opposed haptic means extending upwardly at an angle from the edges thereof, the haptic means having some degree of resilience. Means are included on the posterior surface of the optic portion adjacent the periphery for captively retaining the haptic means in a flexed position just prior to insertion to reduce the maximum dimension of the lens device. The retaining means are positioned adjacent a pair of axially extending positioning apertures adjacent the periphery. Release of the haptic in the preferred embodiment is accomplished by insertion of a tool through the aperture after insertion of the lens device, or the haptic may be disengaged by a spatula.

Further objects, features and advantages of the invention will become apparent from a reading of the description, when taken in conjunction with the drawings, in which like reference numerals refer to like elements in the several views.

DESCRIPTION OF THE PREFERRED EMBODIMENT

Figure 1:
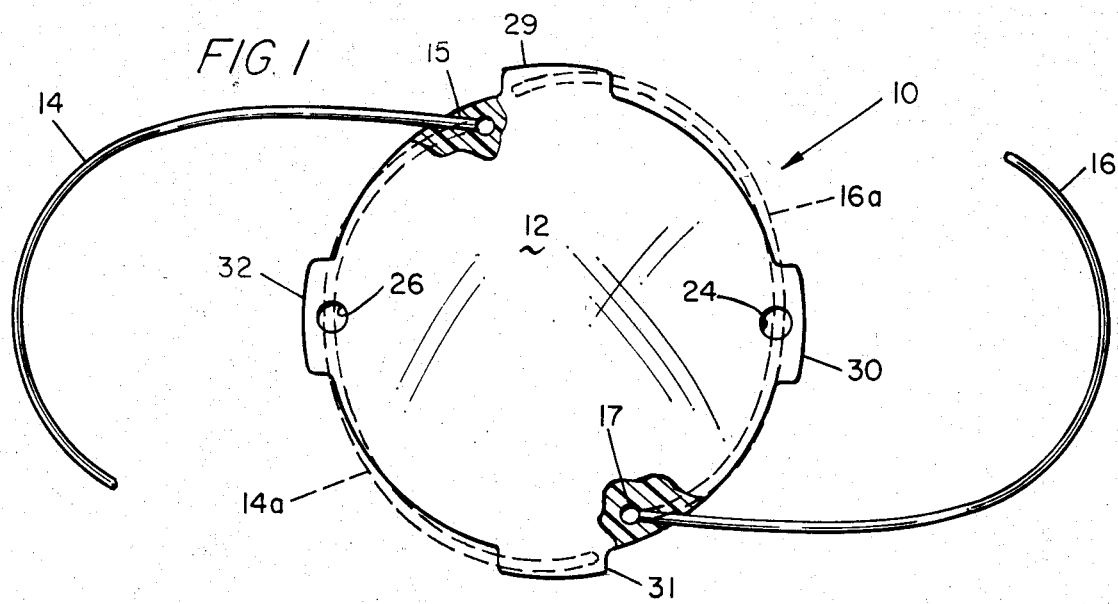
FIG. 1 is a top plan view, partially broken away, of the intraocular lens device according to the invention.
Figure 2:
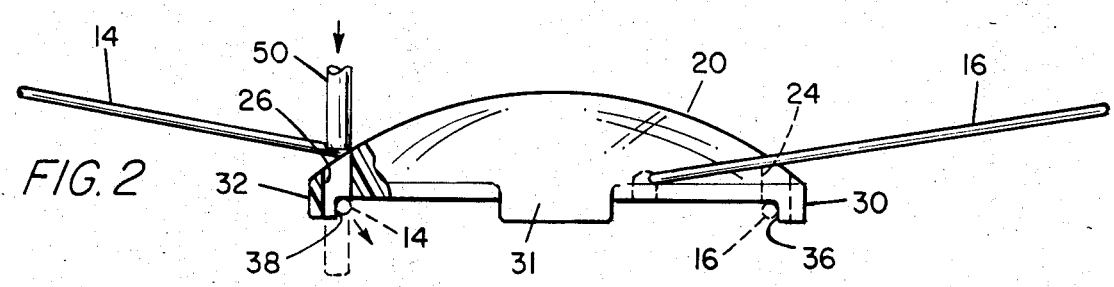
FIG. 2 is a front elevational view, partially broken away, of the intraocular lens device of FIG. 1.

Referring now to the drawings, and particularly to FIGS. 1 and 2, the lens device, generally designated 10, includes a generally plano-convex shaped lens, or optic, 12 with first and second retainers or haptics 14 and 16 extending from opposite sides thereof.

The haptics 14 and 16 are generally C-shaped polypropylene members captively secured at the ends 15 and 17 respectively, by any suitable means, such as by embedding in the material from which the optic 12 is formed. At the point of fixation or securing, the ends 15 and 17 extend generally circumferentially relative to the periphery of the optic 12. The haptics 14 and 16 are referred to as modified J-shaped, but may be of a modified C-shaped configuration, either of which may be found in this style of lens, and either term is intended to include the other.

As better illustrated in FIG. 2, the optic 12 has a planar posterior surface 18 and a concave anterior surface 20. Each haptic 14 and 16 extends at an angle to the planar surface 18 upwardly as depicted in FIG. 2. Each of the haptics 14 and 16 is generally resilient, and assists in positioning and retaining the lens device 10 in proper position after insertion. To further assist in positioning, the periphery of the optic 12 includes two axially extending diametrically opposed drill holes or apertures 24, 26, the apertures 24 and 26 extending along a diameter generally extending through the maximum length of the lens device 10.

The periphery of the optic 12 is provided with two pairs of radially extending, diametrically opposed tab portions 29–32, inclusive, the tabs 29–32 being displaced ninety degrees relative to each other, and extending outwardly beyond the circumference of the optic 12. The apertures 24 and 26 are positioned generally centrally relative to the arc or width of the tabs 30 and 32, respectively, with the centers of the apertures 24 and 26 approximately bisecting the circumference of the main portion of the optic 12 (See particularly FIG. 3).

Figure 3:
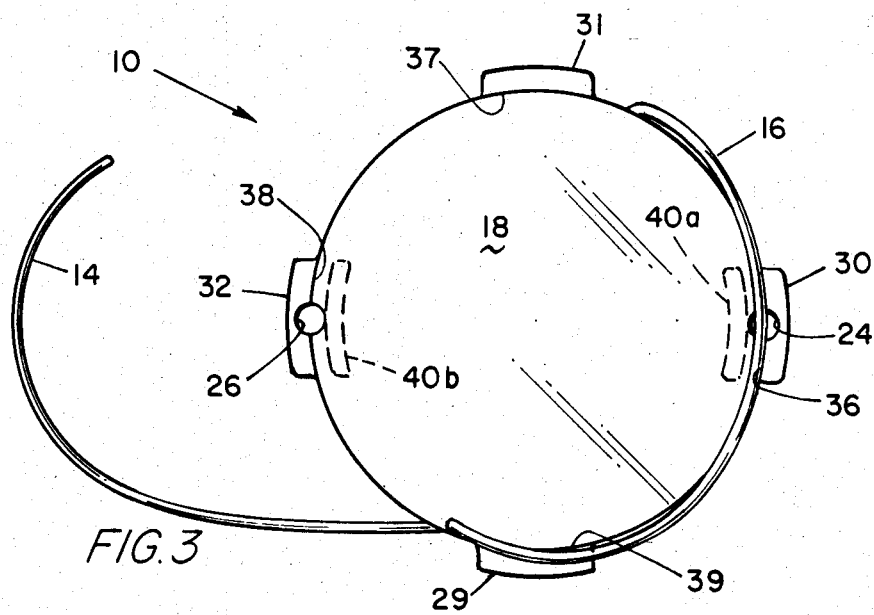
FIG. 3 is a bottom plan view of the intraocular lens device of FIG. 1.

As shown in FIGS. 2 and 3 the posterior surface of the device 10 includes shoulder means, the shoulder means being formed as shoulders 36-39, inclusive, extending generally perpendicularly to the planar surface 18 on the tabs 29-31, respectively. The shoulders 36 and 38 are preferably undercut, which is possible in lathe-formed lens devices. In addition, the shoulders 36-39 define an arc of fifteen to thirty degrees to create shoulders 36-39 with a relatively broad bearing surface to prevent damage to the haptics 14 and 16 which are finely dimensioned. This is especially important with shoulders 36 and 38, which are adapted to retain the haptics 16 and 14, respectively. In addition, the shoulders 36-39 act as spacers between the capsule and the planar portion 18 of the lens or optic 12.

The shoulders 36 and 38 formed in tabs 30 and 32, respectively, are situated, relative to the haptics 14 and 16, at locations which enable the flexing of the haptics 14 and 16 into the positions illustrated in dotted lines in FIG. 1 and designated 14a and 16a, respectively, with the ends retained by the shoulders 38 and 36, respectively (See also FIGS. 2 and 3).

With the lens device 10 as shown and described, the normal position of the haptics 14 and 16 is as illustrated in solid lines in FIG. 1. Prior to insertion of the device 10 into the patient's eye, the haptics 14 and 16 are flexed to the dotted line positions 14a and 16a, with the free ends retained behind the respective shoulders 38 and 36. In FIG. 3, the haptic 16 is illustrated in its flexed position retained by shoulder 36. After insertion, a suitable device such as an instrument 50 is inserted through the aperture 24, as shown in FIG. 2, and with downward pressure, dislodges the haptic 14 (shown in dotted lines) from its retained position, thereby allowing it to return to the original outwardly extending position. By providing these means for retaining the haptics in an inwardly flexed position, the overall dimensions of the lens device are effectively reduced during insertion, thus permitting ready insertion, whether the pupil is dilated or not. Furthermore, the positioning of the apertures 24 and 26 with the centers thereof on the circumference of the optic 12, and the shoulders 36 and 38 being in line with these centers enables ready dislodging after insertion with one hand of the surgeon, and with a simple instrument such as a Sinskey hook, commonly used by surgeons in such implant operations.

Figure 4:
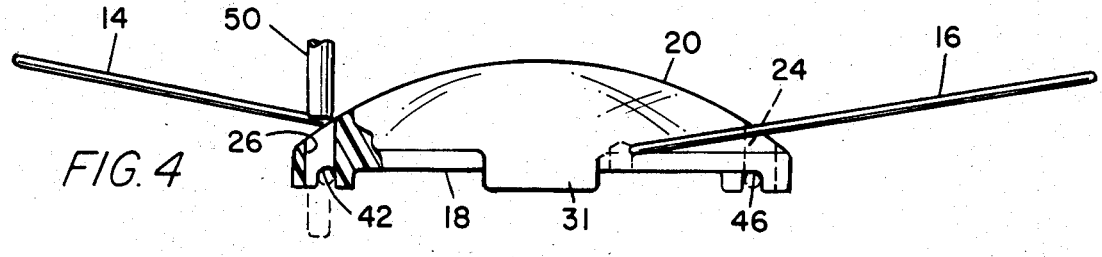
FIG. 4 is a front elevational view of an alternate embodiment of the lens device of FIG. 1.

FIG. 4 illustrates a modified embodiment in which the posterior surface 18 is provided with slots 40 and 42 for captively retaining the haptics 16 and 14, respectively. By referring also to FIG. 3, these slots 40 and 42 may be formed by adding the arcuate segments 40a and 40b, shown in dotted lines, in spaced proximate relation to the shoulders 36 and 38, respectively. The slots 40 and 42 provide for additional frictional engagement of a portion of the haptics 14 and 16.

By way of example, the dimensions of the optic 12 may be 6 mm, with the overall diameter to the edges of tabs 29 and 31 being approximately 6.5 mm. The distance between the outer portions of the haptics 14 and 16 along a diameter of the device 10 is approximately 14 mm. Each of the shoulders 36-39 extends approximately 0.25 mm from the planar surface 18 of the optic 12, with a thickness of 0.35 mm and a width in the circumferential direction of approximately 1.52 mm. With the haptics 14 and 16 captively retained, the largest dimension is reduced from about 14 mm to 9 mm or less, thus facilitating insertion.

Other introcular lenses presently available include haptic means of a "closed loop" configuration, in which both ends of the haptic are secured to the optic in reasonably proximate relation, and such lenses likewise may be configured with means on the optic for retaining the haptic in an inwardly flexed position just prior to insertion. The closer the securement or fixation of the two ends of the haptic, the more the haptic has the tendency to behave as a single strand when being flexed. Furthermore, since the flexing is only for a time duration necessary for insertion, permanent deformation of the haptic does not result.

The preceding description has proceeded with reference to a Shearing style intraocular lens, but it is to be understood that other currently available lenses with haptic means, whether C-shaped, modified C-shaped, J-shaped or closed loop may conveniently employ the haptic retaining means for reducing the overall dimension of the lens device prior to insertion by flexing the haptic means inwardly for retention by means on the optic, with release effected in a suitable manner with a spatula or by use of other instruments.

While there has been shown and described a preferred embodiment it is to be understood that various other adaptations and modifications may readily be made within the spirit and scope of the invention. By way of example, the lens device 10 need not have the tabs 29-31, and the optic 12 may be circular in plan view, that is, as viewed in FIG. 1. The shoulders, or slots may be formed on the posterior surface at positions other than those shown in the drawings, such as at positions adjacent the periphery slightly clockwise from those shown in FIG. 3 to enable gripping at the approximate mid-point of the haptics. The scope of the invention is defined in the appended claims.

I claim:

1. In an intraocular lens device, the combination comprising:
   optic means having an anterior and a posterior surface;
   at least two generally resilient haptic means, said haptic means having at least one end thereof secured to said optic means with said haptic means extending outwardly from the periphery of said optic means; and
   at least two haptic engaging means formed on the posterior surface of said optic means adjacent the periphery thereof for selectively releasably retaining said haptic means in an inwardly flexed position in proximate relation to the periphery of said optic means, said haptic engaging means being positioned for engagement with said haptic means at a position generally intermediate the ends thereof.

2. The combination according to claim 1 wherein said haptic engaging means on said optic means includes slot means.

3. The combination according to claim 2 wherein said haptic means includes first and second generally J-shaped generally diametrically opposed haptics, each having one end thereof secured to said optic means.

4. The combination according to claim 1 wherein said device further includes aperture means through said optic means for enabling insertion of an instrument from the anterior surface to disengage the so-engaged portion of said haptic means from said haptic engaging means on said optic means.

5. The combination according to claim 1 wherein said haptic engaging means on said optic means including shoulder means on the posterior surface thereof.

6. The combination according to claim 5 wherein said device further includes aperture means extending through said optic means in proximity to said shoulder means for enabling insertion of an instrument for disengaging the engaged portion of said haptic means from said shoulder means.

7. The combination according to claim 6 wherein said shoulder means include haptic engaging surfaces and said aperture means have the centers thereof generally coextensive with the plane of said surfaces.

8. The combination according to claim 7 wherein the posterior surface of said optic means is generally planar, and said haptic means engaging surface is generally perpendicular thereto.

9. The combination according to claim 8 wherein said optic means is generally circular in plan elevation and includes at least two radially extending tab means.

10. The combination according to claim 1 wherein said device further includes first and second generally opposed haptic means.

11. The combination according to claim 10 wherein each of said haptic means is generally J-shaped and has only one end thereof secured to said optic means.

12. The combination according to claim 10 wherein said optic means has a generally planar posterior surface and said haptic engaging means on said optic means includes shoulder means extending generally perpendicular thereto.

13. In an intraocular lens device, the combination comprising:

optic means having an anterior and a generally planar posterior surface, said optic means being generally circular in plan elevation and having at least two radially extending tab means;

at least two generally resilient haptic means, said haptic means having at least one end thereof secured to said optic means with said haptic means extending outwardly from the periphery of said optic means;

shoulder means formed on said tab means and including haptic engaging surfaces on the posterior surface of said optic means in generally perpendicular relation to said posterior surface, said haptic engaging surfaces lying generally on the circumference of said optic means for selectively releasably retaining said haptic means in an inwardly flexed position in proximate relation to the periphery of said optic means; and aperture means extending through said optic means and having the centers thereof generally coextensive with the plane of said haptic engaging surfaces for enabling insertion of an instrument therethrough for disengaging the engaged portion of said haptic means from said shoulder means.

14. In an intraocular lens device, the combination comprising:

optic means having an anterior and a posterior surface;

first and second generally opposed generally resilient haptic means, said haptic means having at least one end thereof secured to said optic means with said haptic means extending outwardly from the periphery of said optic means; and slot means on said optic means adjacent the periphery of said optic means for selectively releasably retaining said haptic means in an inwardly flexed position at a point generally intermediate the ends of said haptic means in proximate relation to the periphery of said optic means.

15. The combination according to claim 14 wherein said optic means includes at least two generally diametrically opposed tab means and said slot means are formed on said tab means.

* * * * *